United States Patent
Lo et al.

(10) Patent No.: US 8,380,305 B2
(45) Date of Patent: Feb. 19, 2013

(54) SYSTEM AND METHOD FOR PREDICTING SUCCESSFUL DEFIBRILLATION FOR VENTRICULAR FIBRILLATION CARDIAC ARREST

(75) Inventors: Men-Tzung Lo, Jhongli (TW); Lian-Yu Lin, Taipei (TW); Patrick Chow-In Ko, Taipei (TW); Chen Lin, Jhongli (TW); Matthew Huei-Ming Ma, Taipei (TW)

(73) Assignee: DynaDx Corporation, Mountain View, CA (US)

( * ) Notice: Subject to any disclaimer, the term of this patent is extended or adjusted under 35 U.S.C. 154(b) by 105 days.

(21) Appl. No.: 12/829,286

(22) Filed: Jul. 1, 2010

(65) Prior Publication Data

US 2012/0004693 A1    Jan. 5, 2012

(51) Int. Cl.
*A61N 1/362* (2006.01)
(52) U.S. Cl. .............. 607/5; 600/509; 600/515; 607/6
(58) Field of Classification Search .......... 607/5, 6; 600/509, 515
See application file for complete search history.

(56) References Cited

U.S. PATENT DOCUMENTS

| | | | |
|---|---|---|---|
| 4,610,254 A * | 9/1986 | Morgan et al. | 607/6 |
| 4,619,265 A * | 10/1986 | Morgan et al. | 607/6 |
| 4,989,000 A * | 1/1991 | Chevion et al. | 341/107 |
| 5,092,341 A * | 3/1992 | Kelen | 600/515 |
| 5,109,862 A * | 5/1992 | Kelen et al. | 600/515 |
| 5,571,142 A * | 11/1996 | Brown et al. | 607/5 |
| 5,676,690 A * | 10/1997 | Noren | 607/9 |
| 5,683,424 A * | 11/1997 | Brown et al. | 607/5 |
| 6,438,419 B1 * | 8/2002 | Callaway et al. | 607/5 |
| 6,859,664 B2 | 2/2005 | Daum | |
| 7,231,244 B2 * | 6/2007 | Laitio et al. | 600/509 |
| 7,569,018 B1 | 8/2009 | Geddes | |
| 7,590,443 B2 | 9/2009 | Bharmi | |
| 7,643,877 B2 | 1/2010 | Dujmovic | |
| 7,974,687 B1 * | 7/2011 | Farazi et al. | 600/515 |
| 8,032,213 B1 * | 10/2011 | Qu et al. | 607/7 |
| 2003/0176798 A1 * | 9/2003 | Simon | 600/509 |
| 2005/0131465 A1 * | 6/2005 | Freeman et al. | 607/5 |
| 2006/0270952 A1 * | 11/2006 | Freeman et al. | 601/41 |
| 2007/0244402 A1 * | 10/2007 | Brockway et al. | 600/509 |
| 2008/0046015 A1 * | 2/2008 | Freeman et al. | 607/6 |
| 2008/0188762 A1 * | 8/2008 | John et al. | 600/513 |
| 2008/0188763 A1 * | 8/2008 | John et al. | 600/516 |
| 2008/0208070 A1 * | 8/2008 | Snyder et al. | 600/518 |
| 2008/0312708 A1 * | 12/2008 | Snyder | 607/5 |
| 2009/0037740 A1 * | 2/2009 | Moskowitz | 713/176 |
| 2009/0149903 A1 * | 6/2009 | Freeman | 607/5 |
| 2009/0292180 A1 * | 11/2009 | Mirow | 600/301 |
| 2010/0185225 A1 * | 7/2010 | Albrecht et al. | 606/191 |
| 2011/0112593 A1 * | 5/2011 | Freeman et al. | 607/6 |
| 2011/0118800 A1 * | 5/2011 | Sullivan | 607/5 |

* cited by examiner

*Primary Examiner* — Niketa Patel
*Assistant Examiner* — Christopher A Flory
(74) *Attorney, Agent, or Firm* — SV Patent Service

(57) ABSTRACT

A computer-assisted method for quantitative characterization and treatment of ventricular fibrillation includes acquiring a time series of a ventricular fibrillation (VF) signal using a probe from a patient experiencing VF, subtracting the mean from the time series of the VF signal, calculating a cumulative VF signal after the mean is subtracted from the time series of the VF signal, segmenting the cumulative VF signal by a plurality of sampling boxes, calculating the root-mean-square of the cumulative VF signal as a function of the sampling box size, extracting an exponent of the root-mean-square of the cumulative VF signal as a function of the sampling box size, applying electrical defibrillation to the patient if the exponent is below a predetermined value, and applying cardiopulmonary resuscitation (CPR) to the patient if the exponent is above a predetermined value.

15 Claims, 6 Drawing Sheets

SYSTEM AND METHOD FOR PREDICTING SUCCESSFUL DEFIBRILLATION FOR VENTRICULAR FIBRILLATION CARDIAC ARREST

BACKGROUND

Ventricular fibrillation (VF) is the most common arrhythmia causing sudden cardiac death. Electrical defibrillation remains the method of choice for the treatment of VF. However, the probability of a successful defibrillation decreases after a prolonged duration of VF. Adequate coronary perfusion during cardiopulmonary resuscitation (CPR) is crucial for successful defibrillation following a prolonged VF (or late VF). Studies have demonstrated that a brief period of myocardial perfusion with CPR before defibrillation could improve outcome for selected patients in whom defibrillation is not likely to succeed.

Since out-of-hospital cardiac arrest (OOHCA) does not allow invasive measurement of coronary perfusion status, noninvasive methods have been developed to monitor coronary perfusion status. One such method is based on the VF waveform of surface electrocardiogram (ECG). However, there remains a need to rapidly distinguish early VF and late VF so as to provide timely guidance on the CPR and electrical defibrillation treatments to the patient.

SUMMARY OF THE INVENTION

The systems and methods described in the present application can rapidly and quantitatively distinguish early stage and the late stage of ventricular fibrillation, which can provide timely guidance to the medical personnel on the most effective treatments to patients suffering from ventricular fibrillation. Specifically, the disclosed methods can help medical personnel to determine when CPR is needed, and whether to apply electrical defibrillation in accordance to the stage of the VF. The disclosed systems and methods are non-invasive, and can be conveniently applied in OOHCA. The disclosed systems and methods do not interfere with the CPR treatment, and can thus be applied in conjunction with CPR to increase the rate of successful defibrillation in ventricular fibrillation cardiac arrest.

In a general aspect, the present invention relates to a computer-assisted method for quantitative characterization and treatment of ventricular fibrillation. The method includes acquiring a time series of a ventricular fibrillation (VF) signal using a probe from a patient; subtracting the mean from the time series of the VF signal; calculating a cumulative VF signal by a computer system after the mean is subtracted from the time series of the VF signal; segmenting the cumulative VF signal by a plurality of sampling boxes by the computer system; calculating the root-mean-square of the cumulative VF signal as a function of the sampling box size by the computer system; extracting, by the computer system, an exponent of the root-mean-square of the cumulative VF signal as a function of the sampling box size; applying electrical defibrillation to the patient if the exponent is below a predetermined value; and applying cardiopulmonary resuscitation (CPR) to the patient if the exponent is above a predetermined value. The algorithm of the computer system described here is called Detrended Fluctuation Analysis (DFA).

Implementations of the system may include one or more of the following. The computer-assisted method can further include applying electrical defibrillation to the patient after the step of applying CPR to the patient. The VF signal can include a surface electrocardiogram (ECG) signal. The step of calculating root-mean-square of the cumulative VF signal can include calculating a trend in the cumulative VF signal in each of the plurality of sampling boxes; and subtracting the trend from the cumulative VF signal in each of the plurality of sampling boxes to produce a detrended cumulative VF signal, wherein the root-mean-square of the detrended cumulative VF signal is calculated. The trend in a sampling box can be a linear line with the least square fit to the cumulative VF signal in that sampling box. The computer-assisted method can further include identifying a first region and a second region in the detrended cumulative VF signal separated by a crossover point, wherein the detrended cumulative VF signal in the first region and the second region have different exponents as a function of the sampling box size. The second region can have larger sampling box sizes than the first region. The step of extracting an exponent of the root-mean-square of the detrended cumulative VF signal an include computing the exponent in the second region of the detrended cumulative VF signal. The exponent in the first region can be larger than the exponent in the second region.

In another general aspect, the present invention relates to a computer-assisted method for quantitative characterization and treatment of ventricular fibrillation. The method includes applying cardiopulmonary resuscitation (CPR) to a patient; acquiring a time series of a ventricular fibrillation (VF) signal using a probe from the patient during CPR; subtracting the mean from the time series of the VF signal; calculating a cumulative VF signal by a computer system after the mean is subtracted from the time series of the VF signal; segmenting the cumulative VF signal by a plurality of sampling boxes by the computer system; calculating the root-mean-square of the cumulative VF signal as a function of the sampling box size by the computer system; extracting, by the computer system, an exponent of the root-mean-square of the cumulative VF signal as a function of the sampling box size; and applying electrical defibrillation to the patient if the exponent decreases in response to the CPR.

Implementations of the system may include one or more of the following. The VF signal can include a surface electrocardiogram (ECG) signal. The step of calculating root-mean-square of the cumulative VF signal can include calculating a trend in the cumulative VF signal in each of the plurality of sampling boxes; and subtracting the trend from the cumulative VF signal in each of the plurality of sampling boxes to produce a detrended cumulative VF signal, wherein the root-mean-square of the detrended cumulative VF signal is calculated. The computer-assisted method can further include identifying a first region and a second region separated by a crossover point in the detrended cumulative VF signal, wherein the detrended cumulative VF signal in the first region and the second region have different exponents as a function of the sampling box size. The second region can have larger sampling box sizes than the first region. The exponent can be extracted from the root-mean-square of the detrended cumulative VF signal in the second region. The exponent in the first region can be larger than the exponent in the second region. The electrical defibrillation can be applied to the patient if the exponent decreases by 0.1 or more in response to the CPR.

In another general aspect, the present invention relates to a system for quantitative characterization and treatment of ventricular fibrillation. The system includes a probe configured to acquire a time series of a ventricular fibrillation (VF) signal using a probe from a patient; and a computer processor in communication with the probe. The computer processor can subtract the mean from the time series of the VF signal, calculate a cumulative VF signal after the mean is subtracted from the time series of the VF signal, segment the cumulative VF signal by a plurality of sampling boxes, calculate the root-mean-square of the cumulative VF signal as a function of the sampling box size, and extract an exponent of the root-mean-square of the cumulative VF signal as a function of the sampling box size. The computer processor can recommend electrical defibrillation to the patient if the exponent is below a predetermined value. The computer processor can recommend application of cardiopulmonary resuscitation (CPR) to the patient if the exponent is above a predetermined value.

Implementations of the system may include one or more of the following. The system can recommend electrical defibrillation to the patient after the application of CPR to the patient if the exponent is above the predetermined value. The computer system can calculate a trend in the cumulative VF signal in each of the plurality of sampling boxes and to subtract the trend from the cumulative VF signal in each of the plurality of sampling boxes to produce a detrended cumulative VF signal. The root-mean-square of the detrended cumulative VF signal can be calculated. The computer system can identify a first region and a second region in the detrended cumulative VF signal, wherein the second region has larger sampling box sizes than the first region, wherein the detrended cumulative VF signal has a larger exponent in the first region than in the second region. The computer system can extract the exponent of the root-mean-square of the detrended cumulative VF signal in the second region. The system can further include a display device configured to display the detrended cumulative VF signal as a function of the sampling box size. The probe can record the VF signal from the patient during a CPR applied to the patient. The computer system can extract the exponent of the root-mean-square of the cumulative VF signal during the CPR. The system can recommend electrical defibrillation to the patient after the application of CPR to the patient if the exponent decreases in response to the CPR.

Although the invention has been particularly shown and described with reference to multiple embodiments, it will be understood by persons skilled in the relevant art that various changes in form and details can be made therein without departing from the spirit and scope of the invention.

BRIEF DESCRIPTION OF THE DRAWINGS

The following drawings, which are incorporated in and form a part of the specification, illustrate embodiments of the present invention and, together with the description, serve to explain the principles of the invention.

DETAILED DESCRIPTION OF THE INVENTION

Figure 1:
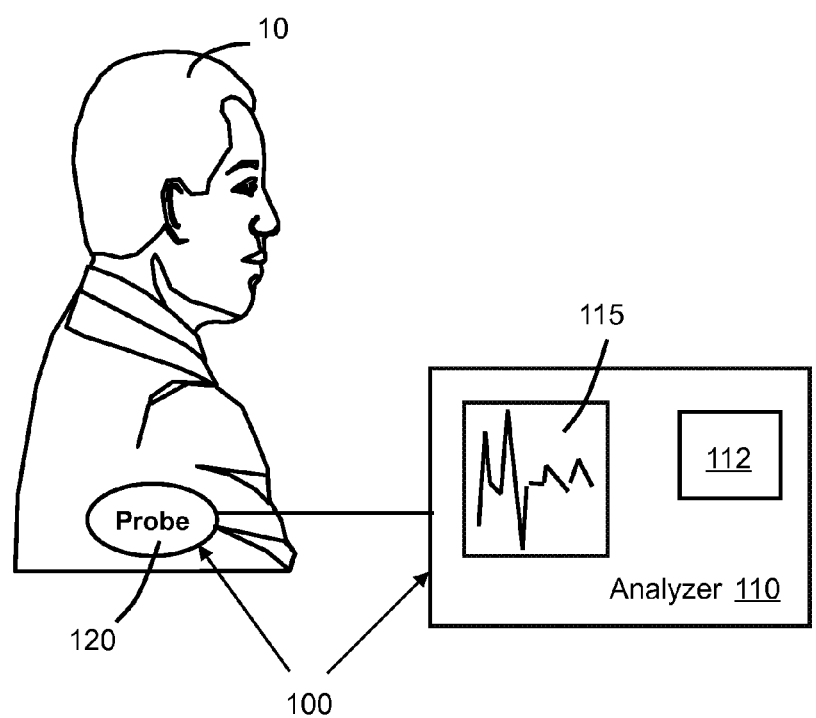
FIG. 1 is a schematic diagram illustrating a system for evaluating ventricular fibrillation in accordance to the present invention.

Referring to FIG. 1, a VF evaluation system 100 includes an analyzer 110 and a probe 120 that can be attached to a patient 10. The probe 120 can include a sensor, a transducer, or an electrode (e.g. in a Holter monitor) configured to measure VF signals from the patient 10. An example of the VF signals is the surface ECG signal. Other examples of the VF signals can include blood pressure and sensing signals obtained by a pulse oximeter. The probe 120 can send the VF signals to the analyzer 110, often in analog form. The analyzer 110 can include an analog-to-digital (A/D) converter for digitizing the VF signals. The analyzer 110 also includes a computer processor 112 that is configured to process and analyze the VF signals after the VF signals are digitized by the A/D converter. A pre-stored algorithm in the analyzer 110 can rapidly analyze the VF signals, and provide guidance to defibrillation treatments, as described in more detail below. The analyzer 110 can also include necessary input/output devices, and a display 115 for displaying the VF signals and the results of the analysis of the VF signals.

Figure 2:
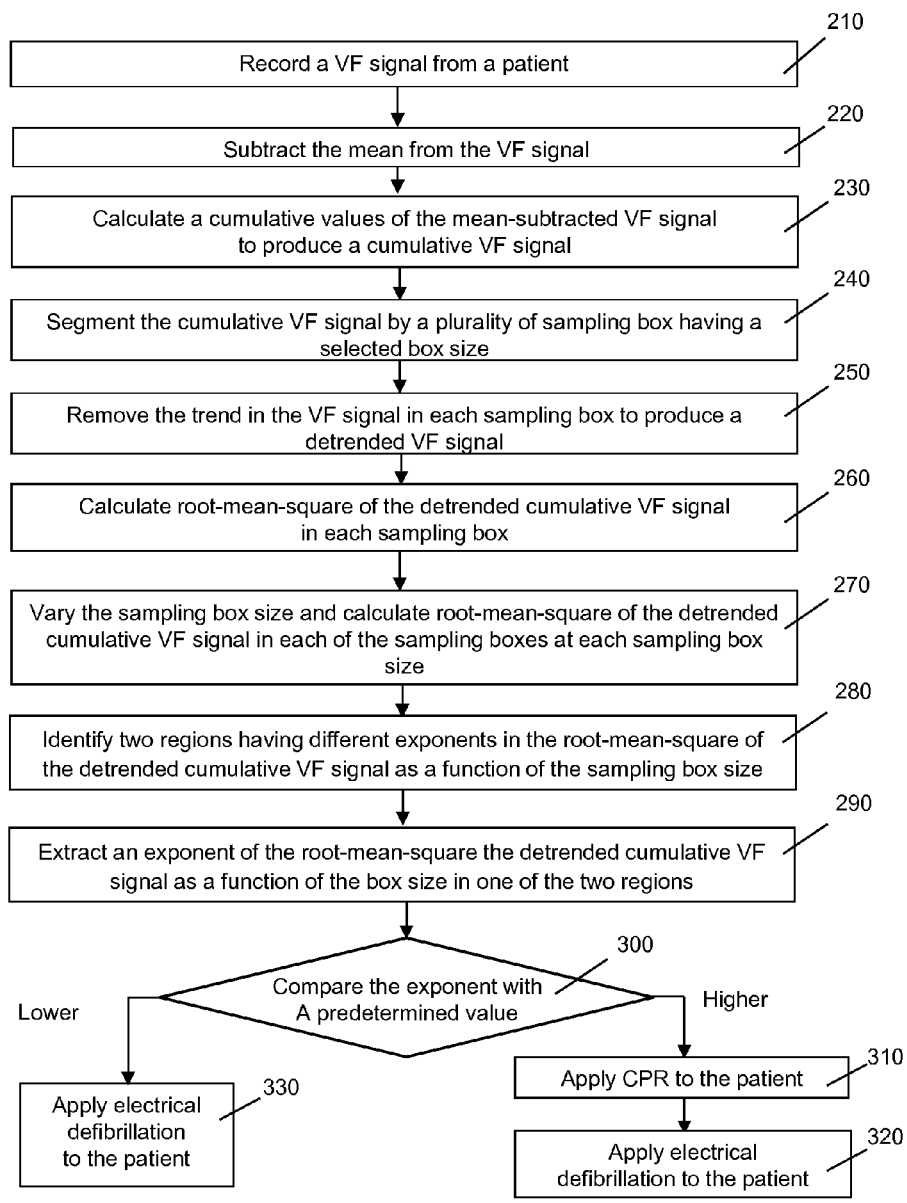
FIG. 2 is a flow diagram illustrating the steps of evaluating ventricular fibrillation for defibrillation treatment in accordance to an aspect of the present invention.
Figure 3A:
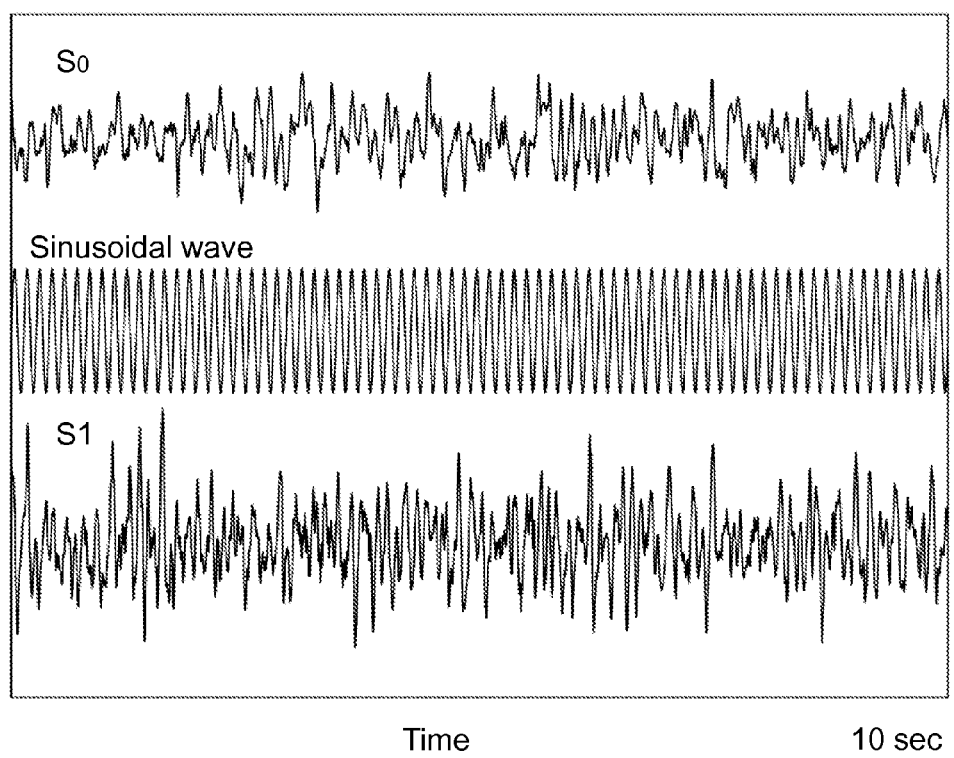
FIG. 3A shows a non-shockable ventricular fibrillation waveform (S0), a shockable ventricular fibrillation waveform (S1), and a sinusoidal wave at a similar oscillation frequency.

In some embodiments, referring to FIG. 2, a time series of a VF signal is recorded using the VF evaluation system 100 from the patient 10 suffering from ventricular fibrillation (step 210). The VF signal can be acquired using the probe 120 in the VF evaluation system 100 (FIG. 1). The VF signal can for example be a surface ECG signal. FIG. 3A illustrates two exemplified VF signals: a non-shockable VF signal waveform (S0) and a shockable VF waveform (S1). A non-shockable VF waveform is a persisted VF or asystole after defibrillation. As a reference for data analysis, a sinusoidal wave having a similar oscillation frequency is also shown in FIG. 3A.

In our analysis, it is conceptualized that VF signals are generated by multiple interacting systems within the heart in a complex but nonrandom process. Analytical methods from the field of nonlinear dynamics are adopted to describe the underlying structure of non periodic but deterministic data series. Specifically, the VF signals are analyzed using detrended fluctuation analysis (DFA) by the analyzer 110 (FIG. 1). The DFA is a scaling analysis method that aims to reveal the correlation properties of a signal. The advantages of the DFA method are that it can detect long-range correlations embedded in seemingly nonstationary waveforms, while also avoiding spurious correlations of non-stationary artifact.

In the analysis by the analyzer 110 (FIG. 1), a mean value of the VF signal is calculated and subtracted from the time series of the VF signal (step 220). The cumulative value of the time series of the mean-subtracted VF signal is calculated to produce a cumulative VF signal (step 230). A sampling box size is selected. The time series of cumulative VF signal is segmented into a plurality of sampling boxes having the selected box size (step 240). In the present application, the term "sampling box" or "box" refers to an interval that is used to segment a period in a VF signal. A trend line is computed in the plurality of sampling boxes having the selected box size (step 250). For example, a trend line in a sampling box can be a linear line with the least square fit to the VF waveform in that sampling box. The trend line is then subtracted from the cumulative VF signal in the sampling box to produce a detrended cumulative VF signal (step 250).

A root-mean-square value is then computed for the detrended cumulative VF signal in each of sampling boxes (step 260). The sampling box size is then varied to a different value (step 270). Root-mean-square values are computed for the detrended cumulative VF signal in each of the sampling boxes having the new box size (step 270). The steps 220-260 are repeated to produce root-mean-square values of the detrended cumulative VF signal as a function of sampling box size, as shown (e.g. S0 and S1) in FIG. 3A. The root-mean-square values of the detrended cumulative VF signal (i.e. the DFA curves) can be plotted as a function of sampling box size in a logarithmic scale.

Figure 3B:
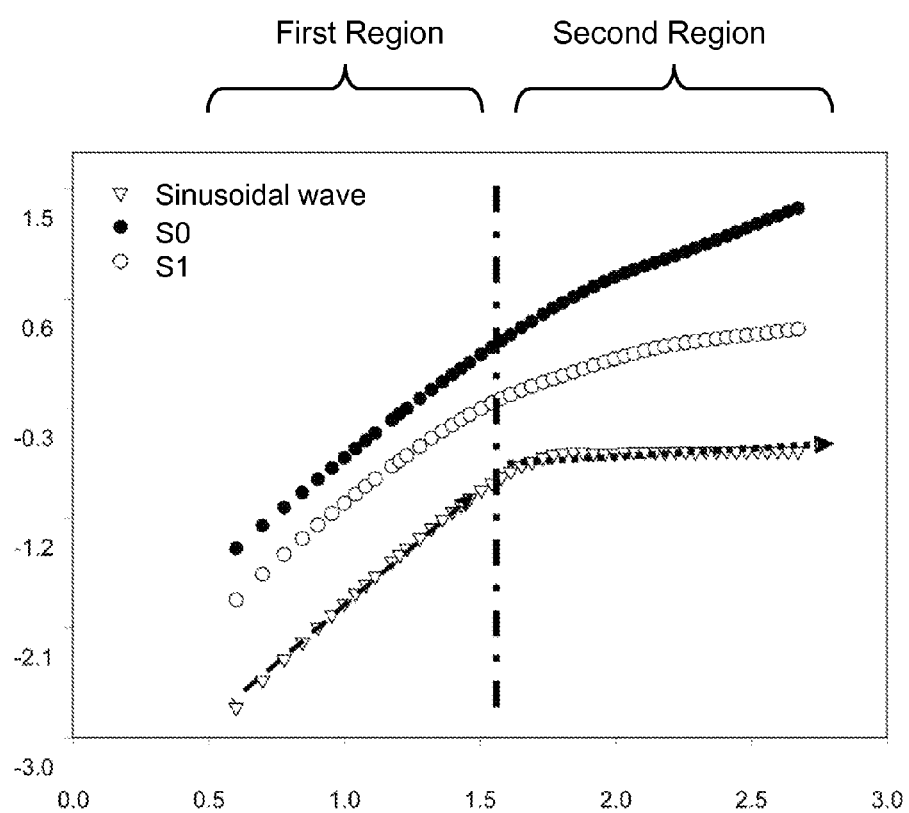
FIG. 3B illustrates the detrended fluctuation analysis (DFA) of the waveforms shown in FIG. 3A, plotted against the sampling box size.

Referring to FIG. 3B, the shockable VF signal (S1) results in lower DFA values over a range of sampling box sizes. The non-shockable VF signal (S0) has higher DFA values. Thus higher DFA values appear to correlate with non-shockable VF signals in late VF. The sampling box sizes are in unit of sampling points. In the data show in FIGS. 3A and 3B, for example, the VF signal can be sampled at 200 points per second resulting in 2000 sampling points in 10 seconds. The DFA values can be plotted in a range of about 5 to 500 sampling points in FIG. 3B. Two regions are identified in the DFA curves (step 280). The sinusoidal wave has lower root-mean-square values and exhibits a crossover between a first region with smaller box sizes and a second region with larger box sizes. The second region can have box size ranging from about 60 sampling points to 250 sampling points.

In accordance with the present invention, referring back to FIG. 2, a slope $\alpha 2$ is extracted from in the second region of the DFA curves (step 290). A slope $\alpha 1$ (or exponent DFA$\alpha 1$) is extracted from in the first region of the DFA curves. In our analysis, DFA$\alpha 2$ is found to be lower than the DFA$\alpha 1$. The slope $\alpha 2$ approaches zero at large box sizes for sinusoidal waveforms. The crossover point is the crossover point corresponds to a sampling box size of about 80. Since the data are plotted in a logarithmic scale, the slope in the data represents the exponent, thus the scaling properties, of the DFA curves as a function of the sampling box size (i.e. with the sampling box size as the base of the exponent). The slopes a1 and $\alpha 2$ are also referred to as the exponent DFA$\alpha 1$ and DFA$\alpha 2$. The DFA curves of VF signals S1 and S0 exhibit linear trends having similar slope as the sinusoidal wave in the first region. In the second region, the DFA curve of non-shockable VF signal S0 has a higher slope $\alpha 2$ than the DFA curve of shockable VF signal S1, while both of which are higher than the slope $\alpha 2$ for the sinusoidal wave. Thus higher slope in the second region of the DFA curve appears to correlate with non-shockable VF signals in late VF.

Mechanism

The electrocardiogram recorded from the surface of the body represents the superposition of the electrical fields generated by different volume elements of the heart. Thus the patterns in the VF signal are likely related to the underlying organization of the myocardial electrical activities. The presently disclosed analysis has identified several different VF phases ranging from large periodic waveforms in the early VF to infrequent episodic electric activities within a segment of myocardium failing to conduct to adjacent segments. It is observed that the second slope $\alpha 2$ is related to the VF conditions in a patient. It is observed that in early VF, few large periodic waveforms render the surface ECG similar to a sinusoidal wave, characterized by a low slope $\alpha 2$. In late VF, the waveforms break and degenerate into small infrequent electric activities, resulting in higher slope $\alpha 2$. In other words, the slope $\alpha 2$ increases as VF worsens over time. The slope $\alpha 2$ or DFA$\alpha 2$ can therefore be used to help medical personnel rapidly quantify the organization property of VF signals in an emergency response to a patient suffering VF.

Validation

Figure 4A:
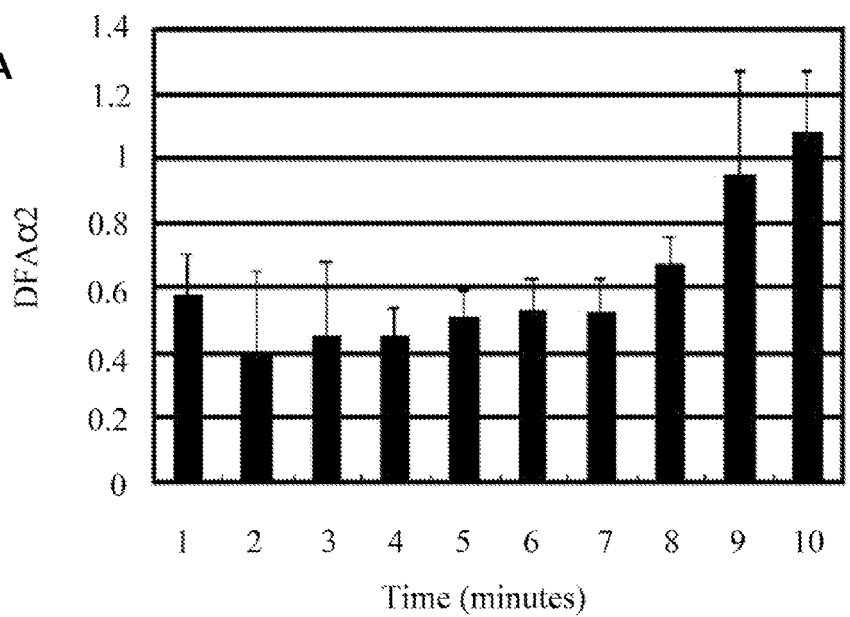
FIG. 4A shows the time evolution of the second exponent $\alpha 2$ of the DFA (DFA$\alpha 2$) computed using VF signals obtained from six patients who experiencing VF.

The mechanism of the previously described observations is validated with clinical data. FIG. 4A shows the time evolution of the second slope $\alpha 2$ (exponent DFA$\alpha 2$) in the root-mean-square of cumulative detrended VF signals obtained from six VF patients. The VF signals are surface ECG signals collected by Holter sensors from the patients in a 10 min period, provided by Physionet (a resource for biomedical research and development sponsored by the National Institute of Biomedical Imaging and Bioengineering and the National Institute of General Medical Sciences in the National Institutes of Health).

Figure 4B:
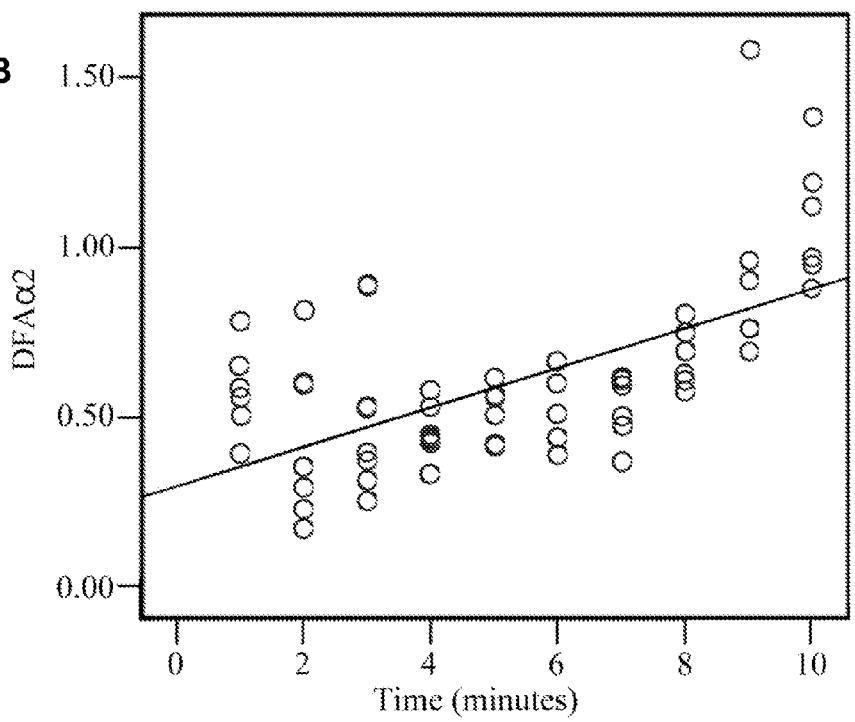
FIG. 4B shows the correlation analysis of the second exponent $\alpha 2$ of the DFA (DFA$\alpha 2$) versus time.

The second slope $\alpha 2$ (exponent DFA$\alpha 2$) is calculated for each 10-second period and averaged every one minute in the entire 10 minute period. FIG. 4A shows the average second slope $\alpha 2$ (DFA$\alpha 2$) and their standard deviations in the ten 1-min periods. The average second slope $\alpha 2$ (DFA$\alpha 2$) appears to increase over time as VF worsens, which suggests that the DFA$\alpha 2$ is an indicator (e.g. "a bio-marker") for the worsening of VF, which is consistent with the conceptualized mechanism described above. The time effects of the second slope $\alpha 2$ (DFA$\alpha 2$) are also examined by correlation analysis, as shown in FIG. 4B, which shows a positive correlation ($P<0.001$) between the exponent DFA$\alpha 2$ and time with R squared=0.392. By using ANOVA, DFA$\alpha 1$ ($P=0.022$), and DFA $\alpha 2$ ($P<0.001$) show significant time-related effects.

In accordance with the present invention, referring back to FIG. 2, the exponent DFA $\alpha 2$ is compared to a predetermined threshold value (step 300). For example, the threshold value can for example be about 0.38. If the exponent DFA $\alpha 2$ is higher than the threshold value (as shown by S0 in FIGS. 3A and 3B), the VF is determined to be late stage; defibrillation alone cannot terminate VF. CPR is applied to the patient to re-perfuse the patient's heart (step 310). Optionally, the VF signal is monitored and analyzed in real time during the application of CPR, which may show a decrease in the exponent DFA $\alpha 2$. Electrical defibrillation can subsequently be applied to the patient (step 320). If the exponent DFA $\alpha 2$ is lower than the threshold value (as shown by S1 in FIGS. 3A and 3B), the VF is determined to be early stage. Electrical defibrillation can be immediately applied to the patient (step 330).

Figure 5:
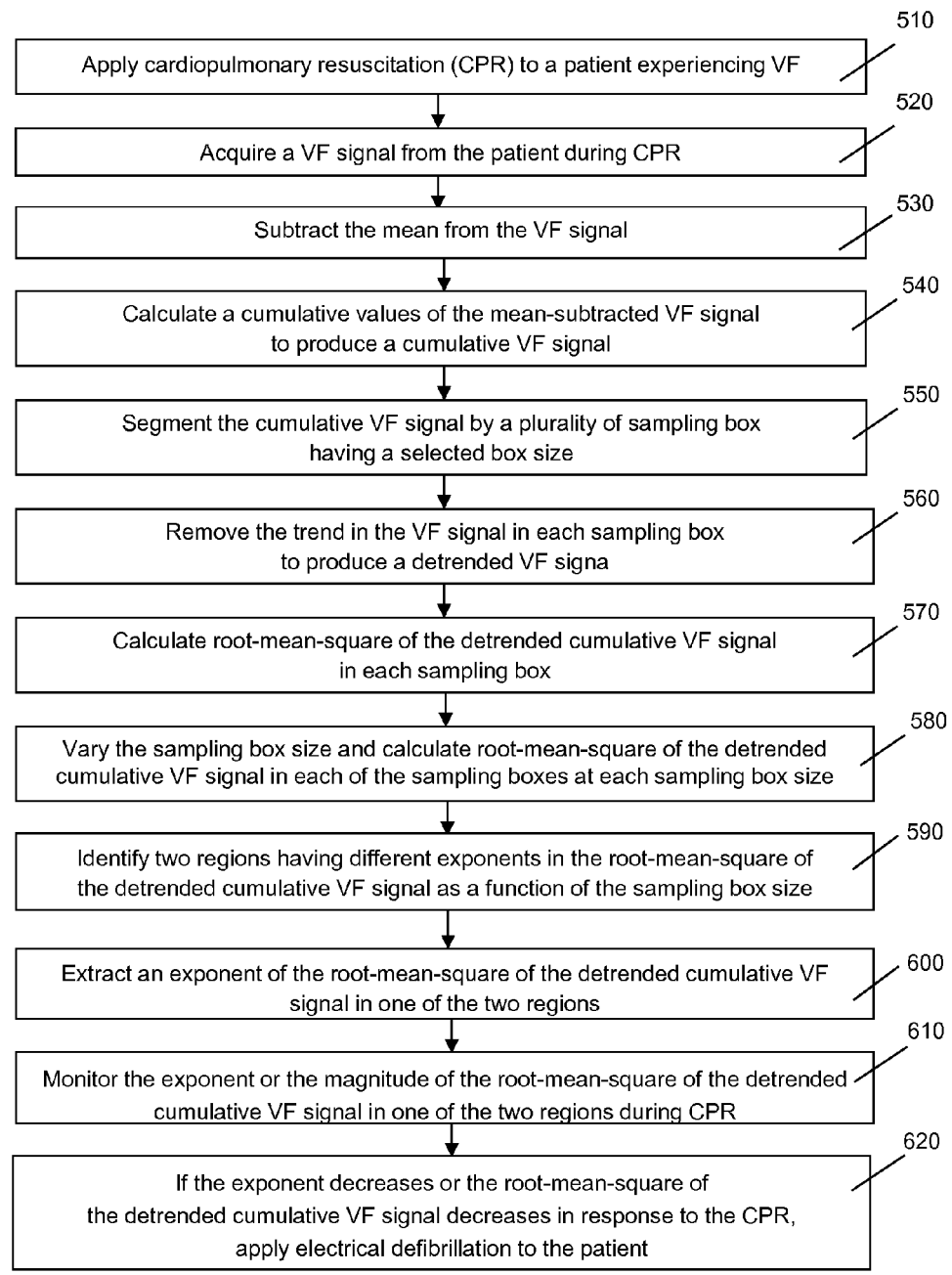
FIG. 5 is a flow diagram illustrating the steps of evaluating ventricular fibrillation for defibrillation treatment in accordance to another aspect of the present invention.

In some embodiments, referring to FIG. 5, CPR is initially applied to a patient experiencing VF (step 510). As an advantage of the presently disclosed system and methods, a VF signal can be acquired non-invasively from the patient during CPR without interfering with the CPR (step 520). The VF signal can be analyzed by the analyzer 110 (FIG. 1) in real time. a mean value of the VF signal is calculated and subtracted from the VF signal (step 530). The cumulative value of the mean-subtracted VF signal is calculated to produce a cumulative VF signal (step 540). A sampling box size is selected. The cumulative VF signal is segmented into a plurality of sampling boxes having the selected box size (step 550). A trend line is computed in the plurality of sampling boxes having the selected box size (step 560). For example, a trend line in a sampling box can be a linear line with the least square fit to the VF waveform in that sampling box. The trend line is then subtracted from the cumulative VF signal in the sampling box to produce a detrended cumulative VF signal (step 560).

A root-mean-square value is then computed for the detrended cumulative VF signal in each of sampling boxes (step 570). The sampling box size is then varied to a different value. Root-mean-square values are computed for the detrended cumulative VF signal in each of the sampling boxes having the new box size (step 580). The steps 530-570 are repeated to produce root-mean-square values of the detrended cumulative VF signal as a function of sampling box size (step 580).

The sampling size is varied. The root-mean-square of the detrended cumulative VF signal (i.e. the DFA curve) is calculated as a function of sampling box sizes (step 580). Two regions having different exponents are identified in the DFA curve (step 590), and the exponents calculated in the two regions (step 600). The second exponent DFA α2 is monitored during the CPR treatment (step 610). If the DFA α2 is found to decrease by more than a predetermined magnitude (e.g. a decrease of 0.1 or 0.2 in DFA α2 ), electrical defibrillation can be applied to the patient (step 620).

Alternatively, the overall magnitude of the detrended root-mean-square curve can be monitored (step 610). If the DFA curve drops in value as a function of the sampling box sizes in the second region, as observed from a display (115, FIG. 1) by a medical personnel, electrical defibrillation is applied to the patient (step 620). In this case, it is optional to calculate the exponent of the DFA signal (i.e. step 590-610 can be skipped). By plotting the DFA curve in real time, CPR can thus be guided not only by a calculated value for the exponent DFA α2, but also the overall shape of the DFA curve. If the DFA curve decreases in its positive slope and (i.e. becomes flatter) in response to the CPR, the likelihood of success for electrical defibrillation is higher. Thus, the DFA curve can help emergency medical personnel more easily visualize and determine the state of VF, which leads to a more correct and faster decision on whether the patients should be defibrillated.

The disclosed system and methods can include one or more of the following advantages. The systems and methods described in the present application can rapidly and quantitatively distinguish early stage and the late stage of ventricular fibrillation, which can provide timely guidance to the medical personnel on the most effective treatments to patients suffering from ventricular fibrillation. Specifically, the disclosed methods can help medical personnel to determine when CPR is needed, and whether to apply electrical defibrillation in accordance to the stage of the VF. The disclosed systems and methods are non-invasive, and can be conveniently applied in OOHCA. The disclosed systems and methods do not interfere with the CPR treatment, and can thus be applied in conjunction with CPR to increase the rate of successful defibrillation in ventricular fibrillation cardiac arrest.

It should be understood that the above described systems and methods are compatible to with different configurations and variations without deviating from the spirit of the present invention. For example, VF signals are not limited to surface ECG waveforms. Moreover, the VF signals can be analyzed in different scaling analyses that can extract exponent versus sampling box size. The VF fluctuations can be characterized by two of more regions each characterized by different exponent. The values for the exponents, the crossover point, and the range for the sampling box sizes can differ from the examples used in the present specification and drawings. Furthermore, different detrending techniques can be used; the trends in sampling boxes can be determined using different approaches.

What is claimed is:

1. A computer-assisted method for quantitative characterization and treatment of ventricular fibrillation, comprising:
   acquiring a time series of a ventricular fibrillation (VF) signal using a probe from a patient;
   subtracting a mean of the time series of the VF signal from the time series of the VF signal;
   calculating a cumulative VF signal by a computer system after the mean is subtracted from the time series of the VF signal;
   segmenting the cumulative VF signal by a plurality of sampling boxes by the computer system;
   calculating a trend in the cumulative VF signal in each of the plurality of sampling boxes;
   subtracting the trend from the cumulative VF signal in each of the plurality of sampling boxes to produce a detrended cumulative VF signal;
   calculating a root-mean-square of the detrended cumulative VF signal as a function of the sampling box size by the computer system;
   identifying a first region and a second region in the detrended cumulative VF signal separated by a crossover point, wherein the detrended cumulative VF signal in the first region and the second region have different exponents as a function of the sampling box size, wherein the second region has larger sampling box sizes than the first region;
   extracting, by the computer system, an exponent of the root-mean-square of the detrended cumulative VF signal in the second region as a function of the sampling box size;
   applying electrical defibrillation to the patient if the exponent is below a predetermined value; and
   applying cardiopulmonary resuscitation (CPR) to the patient if the exponent is above a predetermined value.

2. The computer-assisted method of claim 1, further comprising:
   applying electrical defibrillation to the patient after the step of applying CPR to the patient.

3. The computer-assisted method of claim 1, wherein the VF signal comprises a surface electrocardiogram (ECG) signal.

4. The computer-assisted method of claim 1, wherein the trend in a sampling box is a linear line with the least square fit to the cumulative VF signal in that sampling box.

5. The computer-assisted method of claim 1, wherein the exponent in the first region is larger than the exponent in the second region.

6. A computer-assisted method for quantitative characterization and treatment of ventricular fibrillation, comprising:
   applying cardiopulmonary resuscitation (CPR) to a patient;
   acquiring a time series of a ventricular fibrillation (VF) signal using a probe from the patient during CPR;
   subtracting a mean of the time series of the VF signal from the time series of the VF signal;
   calculating a cumulative VF signal by a computer system after the mean is subtracted from the time series of the VF signal;
   segmenting the cumulative VF signal by a plurality of sampling boxes by the computer system;
   calculating a trend in the cumulative VF signal in each of the plurality of sampling Boxes;
   subtracting the trend from the cumulative VF signal in each of the plurality of sampling boxes to produce a detrended cumulative VF signal;
   calculating a root-mean-square of the detrended cumulative VF signal as a function of the sampling box size by the computer system;
   identifying a first region and a second region separated by a crossover point in the detrended cumulative VF signal, wherein the second region has larger sampling box sizes than the first region;
   extracting, by the computer system, an exponent of the root-mean-square of the detrended cumulative VF signal as a function of the sampling box size in the second region; and
   applying electrical defibrillation to the patient if the exponent decreases in response to the CPR.

7. The computer-assisted method of claim 6, wherein the VF signal comprises a surface electrocardiogram (ECG) signal.

8. The computer-assisted method of claim 6, wherein the detrended cumulative VF signal in the first region and the second region have different exponents as a function of the sampling box size.

9. The computer-assisted method of claim 8, wherein the exponent in the first region is larger than the exponent in the second region.

10. The computer-assisted method of claim 6, wherein electrical defibrillation is applied to the patient if the exponent decreases by 0.1 or more in response to the CPR.

11. A system for quantitative characterization and treatment of ventricular fibrillation, comprising:
 a probe configured to acquire a time series of a ventricular fibrillation (VF) signal using a probe from a patient; and
 a computer processor in communication with the probe, wherein the computer processor is configured to subtract a mean of the time series of the VF signal from the time series of the VF signal, to calculate a cumulative VF signal after the mean is subtracted from the time series of the VF signal, to segment the cumulative VF signal by a plurality of sampling boxes, to calculate a trend in the cumulative VF signal in each of the plurality of sampling boxes and to subtract the trend from the cumulative VF signal in each of the plurality of sampling boxes to produce a detrended cumulative VF signal, to calculate a root-mean-square of the detrended cumulative VF signal as a function of the sampling box size, identify a first region and a second region in the detrended cumulative VF signal, and to extract an exponent of the root-mean-square of the cumulative VF signal in the second region as a function of the sampling box size, wherein the second region has larger sampling box sizes than the first region,
 wherein the computer processor is configured to recommend electrical defibrillation to the patient if the exponent is below a predetermined value, wherein the computer processor is configured to recommend application of cardiopulmonary resuscitation (CPR) to the patient if the exponent is above a predetermined value.

12. The system of claim 11, wherein the system is configured to make recommendation to a medical personnel to apply electrical defibrillation to the patient after the application of CPR to the patient.

13. The system of claim 11, wherein the detrended cumulative VF signal has a larger exponent in the first region than in the second region.

14. The system of claim 11, further comprising a display device configured to display the detrended cumulative VF signal as a function of the sampling box size.

15. The system of claim 11, wherein the probe is configured to record the VF signal from the patient during a CPR applied to the patient, wherein the computer system is configured to extract the exponent of the root-mean-square of the cumulative VF signal during the CPR, wherein the system is configured to make recommendation to a medical personnel to apply electrical defibrillation to the patient after the application of CPR to the patient if the exponent decreases in response to the CPR.

* * * * *